United States Patent
Porter et al.

(10) Patent No.: US 7,226,006 B2
(45) Date of Patent: Jun. 5, 2007

(54) TREATMENT OF MUNICIPAL SOLID WASTE

(76) Inventors: John A. Porter, c/o Fairport Engineering Ltd, Market Place, Adlington, Lancashire (GB) PR7 4EZ; Tony Lees, c/o Fairport Engineering Ltd, Market Place, Adlington, Lancashire (GB) PR7 4EZ; Paul A. Fitton, c/o Fairport Engineering Ltd, Market Place, Adlington, Lancashire (GB) Pr7 4EZ ( * ) Notice: Subject to any disclaimer, the term of this patent is extended or adjusted under 35 U.S.C. 154(b) by 216 days.

(21) Appl. No.: 10/513,203
(22) PCT Filed: May 2, 2003
(86) PCT No.: PCT/GB03/01876

§ 371 (c)(1),
(2), (4) Date: Mar. 3, 2005

(87) PCT Pub. No.: WO03/092922

PCT Pub. Date: Nov. 13, 2003

(65) Prior Publication Data

US 2005/0126957 A1 Jun. 16, 2005

(30) Foreign Application Priority Data

May 3, 2002 (GB) ................................. 0210207.7

(51) Int. Cl.
*B02C 19/00* (2006.01)
(52) U.S. Cl. ............................. 241/23; 241/25; 241/65; 241/101.2; 209/3; 209/11
(58) Field of Classification Search ................. 241/65, 241/101.2, DIG. 38, 21, 25, 23, 30; 71/14, 71/901; 422/26, 209; 209/3, 11, 238, 288, 209/930
See application file for complete search history.

(56) References Cited

U.S. PATENT DOCUMENTS

| 5,190,226 A | 3/1993 | Holloway |
| 5,556,445 A | 9/1996 | Quinn et al. |
| 5,795,479 A * | 8/1998 | Vogt et al. .................. 210/603 |

FOREIGN PATENT DOCUMENTS

EP 0 393 231 A 10/1990

* cited by examiner

*Primary Examiner*—Mark Rosenbaum
(74) *Attorney, Agent, or Firm*—Quarles & Brady LLP; Gavin J. Milczarek-Desai

(57) ABSTRACT

An apparatus and process for the separation, recovery and recycling of municipal solid waste (MSW) in which hot water 48 is added to shredded and homogenized MSW 2 as it enters a rotating feed preparation drum 34 equipped with internal lifter blades 36. The blades 36 and rotation of the drum 34 cause mixing and pulping of the MSW before discharge into a rotating thermal processor 56 also equipped with lifter blades 58 and cone section 64, and in which the moist MSW 2 is heated by heating the hot gases in the processor by a flame from burner 62 which converts the moisture in the MSW to steam. The steam permeates through the MSW as it is turned and lifted in the thermal processor 56, causing further pulping. The now cooked and treated MSW 2 is then fed to a conveyor 68 for transportation to a trommel screen for the separation of recyclable components. In a preferred embodiment plugs 70, 72 of MSW are maintained at the exit and entrance to the thermal processor 56 and act to provide a seal to maintain and control the temperature within the thermal processor 56 by reducing the egress of steam therefrom.

28 Claims, 3 Drawing Sheets

TREATMENT OF MUNICIPAL SOLID WASTE

The present invention relates to apparatus and process for the separation, recovery and recycling of municipal solid waste (MSW) and the like.

Traditionally MSW is disposed of by burying it in a landfill site. However, ecologically this is increasingly considered to be undesirable, since recyclable materials such as glass, metal and plastics have not been separated for recycling. Also, decomposing of the waste and leakage of hazardous materials can lead to environmental contamination, for example methane. Sites suitable for landfill are also on the decline and governments are imposing high taxes on the disposal of waste in this manner, in an attempt to control the over use of such sites and to promote safer more environmentally friendly disposal.

It is also known to incinerate MSW, the combustion of MSW produces ash and also noxious fumes which must be contained and further processed to enable their safer disposal. This method has the disadvantage that it is extremely expensive.

It is therefore desirable to provide a process for treating MSW which aids the separation and recovery of inorganic and organic matter, in a more environmentally friendly and less expensive manner.

U.S. Pat. No. 5,190,226 discloses an apparatus and process for the separation, recovery and recycling of MSW. In this process waste which is delivered to a processing site is conveyed directly into a rotating pressure vessel. An internal helix within the vessel splits the bags of waste and once the vessel is full it is closed, sealed and steam is introduced until the required operating pressure and temperature is reached. The operating conditions are maintained for the required length of time, by regulating the steam input. During this process the cellulosic waste amongst the MSW becomes homogenised by steam saturation and the pulping action of the rotating vessel. Once the cycle is complete, the vessel is depressurised, the steam is removed and the rotation of the vessel is reversed to emit the processed contents thereof on to a conveyor. The conveyor then moves the waste into a rotating trommel, where the pulp falls through the rotating screen onto a conveyor. The separated pulp can then be used to produce fuel or compost. The remaining waste within the trommel, then exits the trommel onto a conveyor for separation of recyclable material and with the remainder going to landfill.

However, the use of a pressure vessel has the disadvantage that the process is batch and not continuous in that the vessel takes 1 to 1½ hours to fill and to bring up to the required temperature, and two further hours for the contents to be mixed at temperature and emptied. Therefore, there is a considerable length of time during which fresh waste cannot enter the pressure vessel. Also, because the vessels are pressurized special safety regulations are enforced for safe operation thereof, which requires considerable skilled man-power, which is unfeasible for smaller processing sites. Furthermore, the gauges on such vessels are not always accurate and pressure may still be relatively high when the vessel is opened, leading to scalding of attendant operators. Furthermore, the vessel also requires a considerable mechanical drive in order to rotate it and in order to discharge its contents at the end of the cycle, with consequential break-down of such mechanisms leading to plant down time and the need to employ skilled service engineers in order to maintain the equipment.

U.S. Pat. No. 5,556,445 (Quinn) describes a process for the treatment of MSW without the use of a pressure vessel. In this process MSW is placed in a perforated drum fixed within a rotatable tube. The interior of the drum is open to the atmosphere. Water is added to the waste and the waste heated by feeding steam between the tube and drum. The rotation of the tube and heating of the MSW causes pulping of the organic matter in the drum, which can then exit the drum through its perforations in order to separate it from the inorganic matter of the waste.

However, this process has the disadvantage that the steam only heats the periphery of the MSW, it is not evenly heated throughout its mass, thereby reducing the efficiency of the process. Furthermore, the organic faction produced has a water content of between 35% to 70%, which is extremely wet and therefore will require further processing to reduce the water content to render the organic faction suitable for use as a composter fuel. Also, some of the putrescible material will not drop through the perforations, causing pegging thereof thereby reducing efficiency and eventually making the process impossible to operate. The MSW does not move through the drum by gravity, but requires internal fins to move the waste out of the drum.

It is an object of the present invention to provide a process and apparatus for the separation, recovery and recycling of MSW that overcomes or alleviates the above described drawbacks.

In accordance with a first aspect of the present invention there is provided an apparatus for treating municipal solid waste (MSW) comprising a moisture supply for adding moisture to said MSW, a non-pressurized feed preparation drum, a non-pressurized thermal processor located downstream of said feed preparation drum, feeding means for conveying moistened MSW to be treated continuously through said drum then said processor, agitating means for mixing the MSW in the feed preparation drum, moisture evaporation means in the processor for substantially turning the moisture in the MSW to steam to cook the MSW, and agitating means for mixing the MSW in the thermal processor. This has the advantage that in a first stage moisture is mixed with the MSW and in a second stage that moisture is turned to steam to cook the MSW reducing any organic matter to a low-moisture pulp and allowing a continuous throughput of MSW.

The drum and processor may be provided in-line in substantially the same plane. This has the advantage that the height of the apparatus can be reduced, with the processor and drum being connected together by for example mechanical seals enabling their independent rotation, or they can be rigidly connected and may comprise separate internal agitation means to independently adjust the speed of mixing in each stage of the process.

The moisture evaporation means is preferably a source of hot gas which heats the hot pulped waste as it is lifted by the agitation means into the hot gas flow and which converts the moisture to steam to pulp and cook the waste and shrink plastics in the waste as the MSW moves down the processor through the mixture of hot gas and steam.

The apparatus may comprise a buffer storage hopper located upstream of the feed preparation drum for receiving MSW to be treated and providing a column of MSW to be fed into the feed preparation drum, the buffer storage hopper having a push floor feeder at its base for directing MSW into the feed preparation drum.

The feed preparation drum may extend or be adapted to extend at a slight angle to the horizontal plane such that its inlet is lower than its outlet. This enables excess moisture in the drum to drain towards the inlet end of the drum, whereat it can be held in a reservoir.

The apparatus may comprise a discharge chamber located between the feed preparation drum and thermal processor for receiving moistened MSW discharged from the feed preparation drum and providing a column of moist MSW to be fed to the thermal processor, the column of moist MSW providing a plug of moist MSW at entrance to the thermal processor, the discharge chamber may have a push floor feeder at its base for directing said moist MSW into the thermal processor.

The apparatus may comprise a thermal processor discharge chamber located downstream of the thermal processor for receiving the cooked MSW from the thermal processor and for providing a column of MSW to be discharged from the apparatus, the column providing a plug of cooked MSW at the outlet to the thermal processor, the thermal processor discharge chamber may have a push floor feeder at its base for directing MSW out of the apparatus.

In a preferred embodiment stocking means are provided for forming a column of MSW at the entrance and/or exit to the thermal processor. The MSW plugs provide a seal at the entrance and/or exit to the thermal processor which enables steam to be retained. Any steam which does permeate back through the apparatus preheats the MSW before entry into the thermal processor and/or feed preparation drum.

The agitating means may be in the form of means for rotating the drum or processor, and may be provided with internal lifting blades. Such means ensure thorough mixing of the moisture/steam within the MSW, induce tearing of the MSW and help to move the MSW through the drum/processor.

The interior of the thermal processor may taper inwardly towards its exit. This has the advantage that as the MSW is reduced in volume by the cooking and pulping thereof the volume fill of the processor is maintained, ensuring that any plastics present in the MSW are heated to induce shrinkage.

In accordance with a second aspect of the present invention there is provided a process for treating municipal solid waste (MSW) comprising the steps of:
  adding moisture to the MSW;
  conveying the MSW through a non-pressurized feed preparation drum;
  agitating said MSW as it is conveyed through the drum to moisten the MSW and to initilize pulping of organic matter present in the MSW;
  conveying the moistened MSW from the drum to a non-pressurized thermal processor;
  agitating said moist MSW as it is conveyed through the thermal processor;
  heating the moist MSW in the processor to substantially turn the moisture to steam to cook the MSW.

The MSW may be stocked upon its entrance into and/or its exit from the thermal processor to provide a plug of MSW at inlet and/or outlet to the thermal processor, this provides a seal at the entrance and/or exit of the thermal processor to help retain the heat therein and maintain the required temperature within.

The MSW may be shredded and homogenized prior to the process in order to reduce the size of waste entering the feed preparation drum, thereby reducing the amount of time required for the process, the size of the drum and processor and reducing potential damage to the apparatus The moisture may be preheated before it is added to the MSW, this increases the efficiency of the feed preparation step before entry into the thermal processor.

The temperature in the thermal processor is preferably raised up to 400° C. at its outlet and up to 100° C. at its inlet, this ensures pulping of the waste. This is higher than the temperatures described in U.S. Pat. No. 5,556,445 (Quinn) whose operating temperature is only in the range of 100° C. to 260° C. The required temperature of the processor may be set to achieve the required degree of cleaning of the waste, in that it may be adjusted to achieve sterilization of the waste, if required. The parameters of the MSW at various stages of the process may be monitored and the measurements used to adjust the flow of MSW.

By way of example only a specific embodiment of the present invention will now be described with reference to the accompanying drawings, in which.

Figure 1:
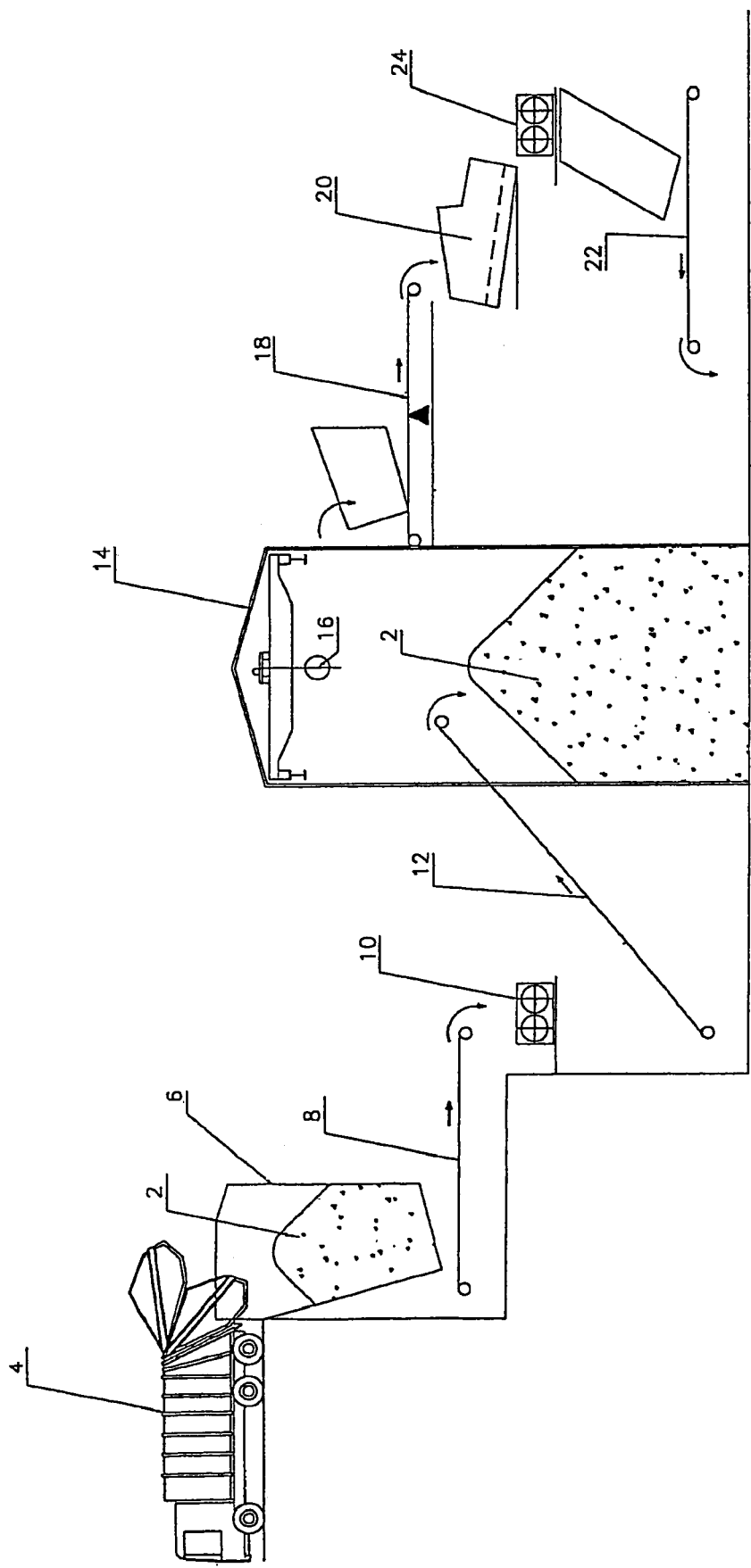
FIG. 1 is a schematic view of municipal solid waste (MSW) collection and feed pre-treatment process adapted in accordance with the present invention.

Referring to FIG. 1 municipal solid waste (MSW) 2 is delivered to a processing plant by for example a refuse vehicle 4 from which it is tipped into a hopper 6 feeding an inspection/picking belt 8. Extremely large items of MSW, such as for example microwave ovens, carpets and bicycles etc may be removed from the MSW at this stage. The remaining MSW on the inspection/picking belt 8 discharges into a primary shredder 10 which tears open bin bags and shreds the waste to items of a width of less than 300 mm. The waste is then conveyed via a conveyor 12 into a waste tipping hall 14 for homogenisation in a known manner.

The waste is collected from the tipping hall 14 using a crane grab 16 operable to enable the deposit of waste into a hopper and belt weigh feeder 18 at a rate of 4000 to 6000 Kg (4 to 6 tonnes) per hour. The feeder 18 feeds a screen 20 through which waste sized at less than 200 mm can fall to a conveyor 22, on which it is conveyed to the next stage of the process described further hereinunder. Waste sized greater than 200 mm is conveyed along the screen 20 and into a secondary shredder 24. The secondary shredder 24 shreds the waste to a size of less than 200 mm and discharges this now further shredded waste down onto said conveyor 22 for transportation to the next stage of the process.

Figure 2:
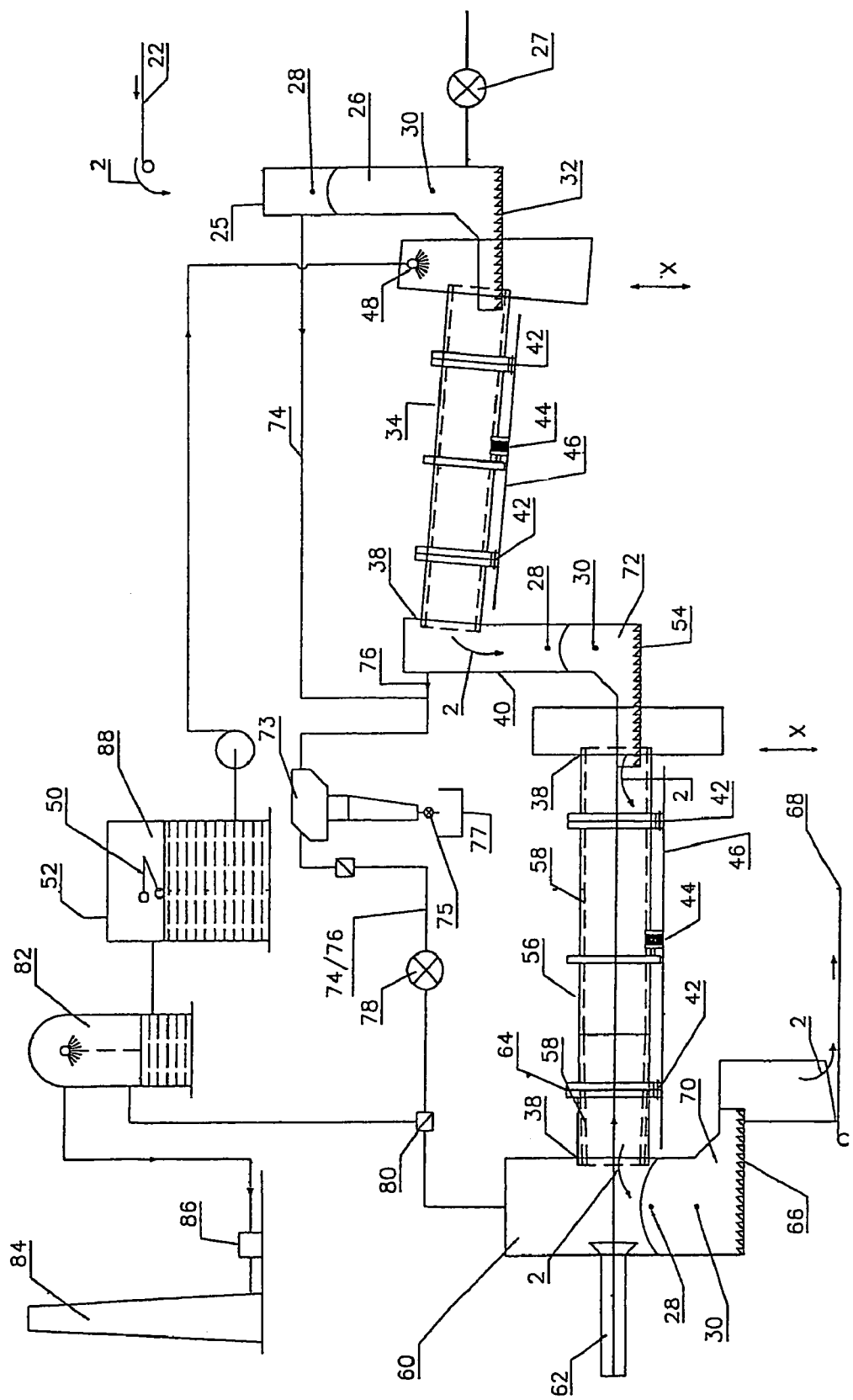
FIG. 2 is a schematic view of an apparatus constructed in accordance with the present invention for treating MSW delivered from the process of FIG. 1.

Conveyor 22 conveys the homogenised shredded waste into the first section of a processing plant, as best illustrated in FIG. 2, comprising a non-pressurized, preheated, thermally clad buffer storage hopper 26 into which the waste is deposited and in which the waste is then preheated by hot air source 27 up to 95° C. High level probe 28 is used to monitor the infeed of waste from the conveyor 22 into the hopper 26, whilst low level probe 30 is used to monitor the outflow of waste from the hopper 26 to the next stage of the process. Measurement from the probes 28, 30 are used to adjust in the input of waste from the conveyor 22 into the hopper 26, in that if the level of waste falls below low level probe 30 additional waste is added to the hopper, and once waste reaches the level of probe 28 the waste input is halted. The entrance to the hopper 26 is fitted with an air lock seal valve 25, which is opened when the waste is input from the conveyor 22 and closed to seal the hopper when the input is ceased. The column of waste in the hopper provides gravity feed assistance to the flow of waste to the next stage of the treatment of the waste, additionally the base of the storage hopper 26 contains a push floor feeder 32 which discharges the waste at a controlled rate from the hopper 26 into the entrance of a feed preparation drum 34. The feed preparation drum comprises a thermally clad rotatable drum with a series of internal lifter blades along its length for lifting, tearing, pulping and advancing the waste material along its length. The feed preparation drum 34 is fitted with mechanical seals 38 at its inlet and outlet ends to enable its rotatable mounting between the inlet hopper 26 and a feed preparation drum outlet/thermal processor inlet chamber 40.

The push floor feeder 32 is designed to fit snugly with the mechanical seal 38 at the entrance to the feed preparation drum 34 and is set at an angle, downwardly inclined towards the entrance to the feed preparation drum 34 to enable a smooth flow of waste material into the drum. The low level probe 30 monitors the waste in this region and enables the control of the feed of the feeder 32 to adjust the flow of waste into the drum 34 in order to prevent blockage thereof.

The drum 34 is rotated on tyres and wheels 42 and is operated through a variable speed chain drive 44 capable of running at a relatively high speed. The drum 34 is tiltable by plus or minus a few degrees X from horizontal by a tilting mechanism 46. The drums drive and the tilting mechanism are controlled based on measurement taken from the probes 28, 30 to facilitate the required throughput of waste.

As the waste passes from the hopper 26 into the wet feed preparation drum 34 it is sprayed at a controlled rate with a mist of water 48 which is supplied from a tank of water 50. The temperature of the water can also be adjusted depending on the detected temperature of the MSW.

Chemical additives 52 which assist with the breakdown of certain components in the waste may be added to the water if required.

Once inside the wet feed preparation drum 34 the waste is lifted by the rotation of the drum 34 and the action of the lifter blades 36 and is thoroughly mixed and pulped as it passes along the length of the drum 34 before discharging into the thermal processor inlet chamber 40. Inlet chamber 40 is equipped with high and low level probes 28 and 30 which monitor the levels of the waste within the inlet chamber 40, and as above are used to adjust the flow of waste.

The base of the chamber 40 is fitted with a further push floor feeder 54 which discharges the waste at a controlled rate from the inlet chamber 40 into a thermal processor 56 and which is disposed and controlled similarly to feeder 32.

The thermal processor 56 comprises a thermally clad rotatable drum with a series of internal lifter blades 58 along its entire length, which lift and advance the waste through the drum as it rotates. The thermal processor 56 is fitted with mechanical seals 38 at each end to enable its rotatable mounting between its inlet chamber 40 and a thermal processor outlet chamber 60 provided at the outlet to the thermal processor 56. The thermal processor 56 is rotated on further tyres and wheels 42 and is operated through a further variable speed chain drive 44 capable of running at a relatively high speed. The thermal processor 56 is tiltable by plus or minus a few degrees X from horizontal by a further tilting mechanism 46. The drive and tilt are adjusted to achieve the required throughput.

A gas burner and air inlet unit 62 is mounted in the outlet chamber 60 whose gas flame output is injected through a baffle spreading can feeding into the discharge end of the thermal processor 56. As the hot pulped waste is fed into the entrance of the thermal processor 56, from the push floor feeder 54, the waste is further lifted by the rotation of the thermal processor 56 and the action of its lifter blades 58 causing further mixing and pulping as it passes along the length of the thermal processor 58 before discharge into the outlet chamber 60. Additionally the gas flame injected into the rotating thermal processor 58 by the gas burner unit 62 heats the air and converts the hot water in the pulped waste into steam raising the temperature at the outlet zone 64 of the thermal processor to between 250° C. to 400° C. and the inlet end 38 to approximately 100° C. The conversion of the moisture in the hot pulped waste into steam further pulps the waste and cooks the waste before its discharge into the outlet chamber 60; with the steam and input air fully permeating the waste as it is lifted and advanced through the thermal processor.

The outlet zone 64 of the thermal processor 58 comprises an internal cone body 64, which gradually tapers towards the outlet chamber 60 to gradually reduce the internal diameter of the thermal processor 58 towards its outlet end 60. This acts to further concentrate the heat in the outlet zone of the thermal processor, as the waste reduces in volume as any cellulosic material is converted into a low moisture pulp and waste such as plastics are shrivelled, and cans and glass scrubbed clean. The volume of the waste is typically reduced in volume up to by 60% by this stage of the process.

The outlet chamber 60 is also fitted with high and low level probes 28 and 30 which as in the previous chambers act to monitor and control the level of the waste therein.

The waste is discharged from the outlet chamber 60 by a further push floor feeder 66 onto a belt conveyor 68 for transfer onto a trommel screen where the waste can be separated into component recyclable parts using conventional equipment in a known manner.

The waste in the outlet chamber 60 is stocked to provide a plug of waste material 70 by controlling the flow of waste using the measurements obtained from the high and low level probes 28 and 30 the column of waste between the probes providing a seal at the outlet to the thermal processor. The waste in the inlet chamber 40 is similarly stocked to provide a plug of higher density waste at the inlet to the thermal processor 58. The throughput of the waste is adjusted by controlling the input of waste into the thermal hopper 26 from the conveyor 22 and by adjusting the speed of operation of the push floor feeds 32, 54 and 66. Furthermore, the speed of rotation of the wet feed preparation drum 34 and thermal processor 56 and their angle of tilt can be adjusted, as well as the amount of water added. The two plugs of waste 70 and 72 at the outlet and inlet ends of the thermal processor 56 act to provide a seal to maintain and control the temperature within the thermal processor, by reducing the egress of steam and heat from the thermal processor 56. The various mechanical seals 38 also act to prevent the egress of steam to the environment.

The outlet chamber 60 is fitted with an explosion vent/disc (not illustrated) at atmospheric pressure to vent explosive gasses, for example if there is a waste gas bottle within the waste which could explode during treatment of the waste, thereby maintaining the thermal processor at substantially atmospheric pressure. The outlet chambers 60 and 40 is further fitted with a temperature gauge (not illustrated) and viewing glass window (not illustrated) to enable an operator to observe the waste treatment and to initiate a manual override if necessary.

Any heat or steam which does permeate upstream of the waste acts to preheat the waste in the wet feed preparation drum 34 and the buffer storage hopper 26. Excess steam and heat is extracted from the buffer storage hopper 26 and the inlet chamber 40 by extraction lines 74 and 76 via the action of extraction fan 78 and damper 80, which latter recirculates the gas/steam back to the outlet chamber 60 and directs any surplus to a scrubber 82 for thermal efficiency. An air separator 73 in the extraction lines removes any films, plastics, or particles entrained in said gas/stream and ejects such via rotary valve 75 into a skip 77. The air lock, slide valve 25 preventing the extraction line merely drawing air from the external environment. The scrubber 82 cleans the waste steam/gas to reduce the emissions before discharge through stack 84 via the action of extractor fan 86, to an acceptable level to meet the environmental regulations. The hot water in the scrubber 82 is then treated with chemicals before it is transferred to the water tank 50 which supplies water 48 to the waste entering the wet feed preparation drum 34. The water tank 50 is additionally supplied with water from a mains supply 88. This gives rise to an environmentally friendly system, in that a substantial portion of the excess heat/moisture is recycled.

Tests on this process and apparatus show that during processing the volume of the waste is reduced to approximately 60% with 85 to 90% of the thermally treated waste suitable for recycling and only an inert residue of 10 to 15% needing to go to landfill (the percentage is dependent on the initial content of the input of MSW to the process). The cooked waste has the following products:

cellulosic pulp having a moisture content of up to 15% which is highly suitable for further processing to produce a fuel or compost;

steel and aluminium cans which have been cleaned and delabelled;

glass bottles which have been cleaned and delabelled;

plastic bottles and bags which have been shrunk and thereby reduced in volume; and inert landfill material.

Figure 3:
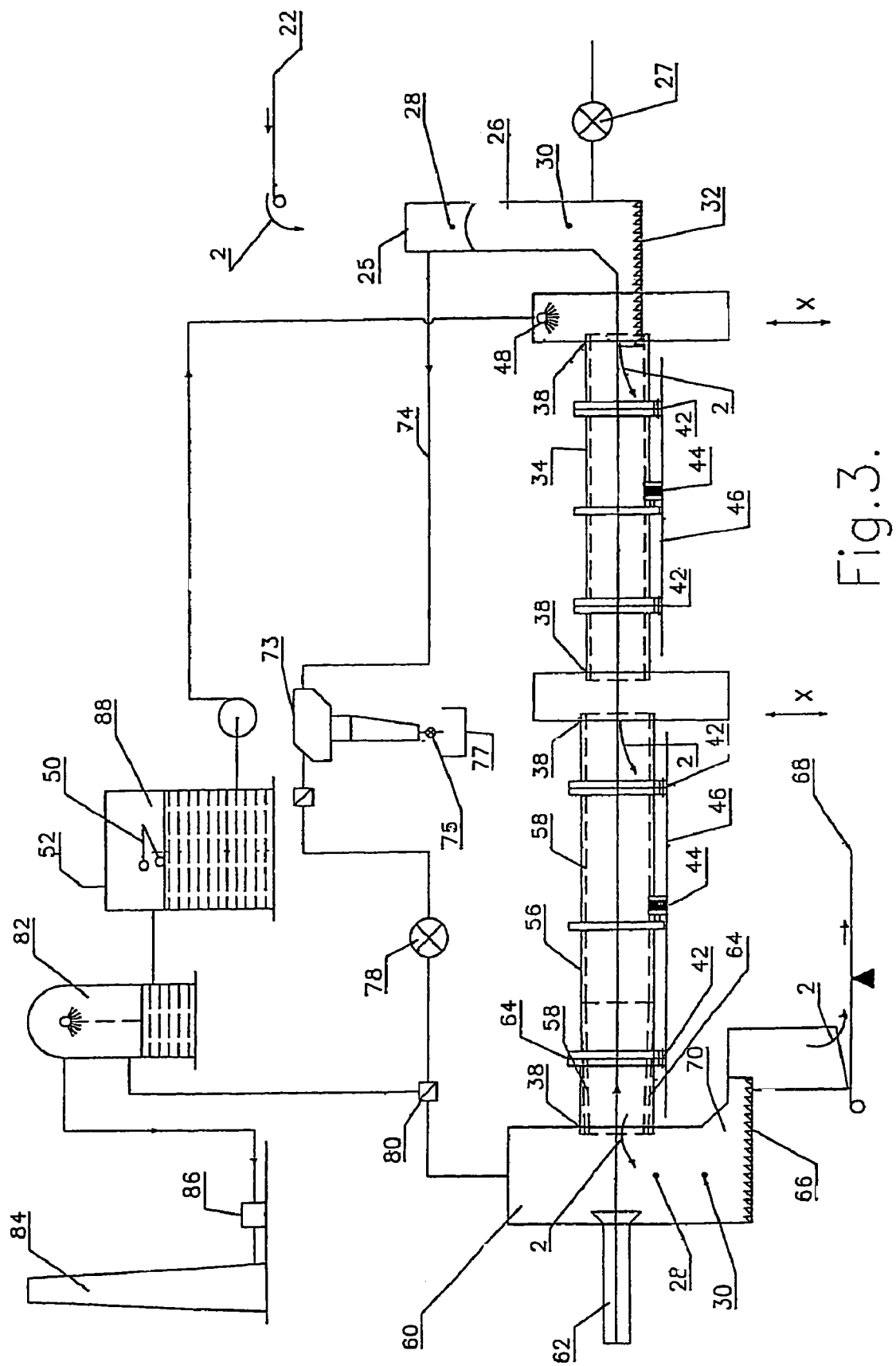
FIG. 3 is a schematic view, similar to that of FIG. 2 of a second embodiment of apparatus for treating MSW.

Although the feed drum and thermal processor have been described as being vertically spaced apart via the interposition of a feed preparation drum outlet/thermal processor inlet chamber 40, it is to be understood that the chamber 40 could be omitted and the drum 34 and processor 56 provided instead directly in-line, as best illustrated in FIG. 3. In this embodiment the drum and processor are interconnected by their mechanical seals 38, the drum 34 by this means feeds the warmed moist waste directly into the thermal processor 56 for cooking and is rotatable independently of the thermal processor 56. The drum 34 in use is turned faster than the processor 56 facilitating complete mixing of the water and waste and initilisation of the pulping process. Although the processor and drum have been described as being directly adjacent, they could be provided in line, but spaced apart by a chamber between their respective mechanical seals through which the waste can pass, without direct agitation. Furthermore, the mechanical seals could be omitted and the drum and processor formed as a unitary chamber, with the preparation of the waste by adding water and agitating taking part in the front end of that chamber, and the cooking taking part downstream thereof at the outlet end to that chamber.

Furthermore, although the feed preparation drum has been illustrated as extending in a horizontal plane, this drum could in an alternative embodiment extend at a slight angle to the horizontal plane, such that its inlet is lower than its outlet. By this means any excess moisture drains towards the inlet to provide a reservoir at the inlet end of the drum. The reservoir providing a source of moisture for the MSW as required. A drain can be provided to remove excess moisture from the reservoir. The backward inclination to the MSW passing through the drain can be selectively provided by the tilting mechanism depending on conditions detected, or can be a permanent feature of the drum by fixing the drum in position at an angle, or by providing an inclination to its internal chamber. The tilting mechanism may be omitted.

It is to be understood that the invention is not limited to the specifically described apparatus and other arrangements will be apparent to one skilled in the art which facilitate a continuous process with thermal cooking and mixing at substantially atmospheric pressure. For example, although the agitation of the waste has been described as being by rotating the drum/processor and via the action of internal fixed lifter blades, other forms of agitation means may be additionally or alternatively provided in that the drum/processor may be fixed and rotatable shredders may be provided inside the drum/processor. Although a gas burner unit has been described as the heat source for converting moisture in the waste to steam, the applied heat could for example be an oil burner or other radiant heat sources. Although heat is injected into the outlet end of the thermal processor, such heat may additionally, or alternatively be injected through the walls of the thermal processor directly, via separate injectors or which may enter via ports provided in the lifter blades or shredders.

Although the plugs 70, 72 of waste have been described as being formed by controlling the rate of flow of waste through the processing plant, a control paddle may be additionally or alternatively provided which is operated to directly stoke the plug to provide the inlet/outlet seal. Although a chemical additive has been described as being added to the water supply, such could be separately added to the waste. Although the waste in the wet feed preparation drum has been described as being heated by adding water and steam permeating back through the system from the thermal processor, additional heating means could be provided. Although an air lock slide valve has been described at the entrance to the hopper, this could be omitted and/or a similar seal provided at the outlet to the outlet chamber 60. Although a cone section has been described at the outlet to the thermal processor, this could be omitted. Although the various vessels have been described as being thermally clad, such may comprise special heat retentive steel or a combination of both. Although the drum and processor have been illustrated as having substantially the same cross-section, they could have different diameters. For example, the drum could have a smaller cross-section than the processor, enabling a greater proportion of hot air and steam within the processor. Although a specific pre-treatment of the waste has been described with reference to FIG. 1, this stage of the treatment could also be varied to provide near consistent quality of shredded homogenized MSW. Also, the treated waste being discharged from the outlet chamber 60 of the thermal processor may be further treated by the addition of water, if for example the cellulosic pulp's end use requires a wetter pulp.

While the invention has been described in detail in terms of a specific embodiment thereof, it will be apparent that various changes and modifications can be made therein by one skilled in the art without departing from the scope thereof.

The invention claimed is:

1. An apparatus for treating municipal solid waste (MSW) comprising a moisture supply for adding moisture to said MSW, a non-pressurized feed preparation drum, a non-pressurized thermal processor located down-stream of said feed preparation drum, feeding means for conveying moistened MSW to be treated continuously through said drum then said processor, agitating means for mixing the MSW in the feed preparation drum, moisture evaporation means in the thermal processor for substantially turning the moisture in the MSW to steam to cook the MSW, and agitating means for mixing the MSW in the thermal processor.

2. An apparatus as claimed in claim 1, wherein the drum and processor are provided in-line in substantially the same plane.

3. An apparatus as claimed in claim 2, comprising a buffer storage hopper located upstream of the feed preparation drum for receiving MSW to be treated and providing a column of MSW to be fed into the feed preparation drum, the buffer storage hopper having a push floor feeder at its base for directing MSW into the feed preparation drum.

4. An apparatus as claimed in claim 2, comprising a discharge chamber located between the feed preparation drum and thermal processor for receiving moistened MSW discharged from the feed preparation drum and providing a plug of moistened MSW at entrance to the thermal processor, the discharge chamber having a push floor feeder at its base for directing said moistened MSW into the thermal processor.

5. An apparatus as claimed in claim 2, comprising a thermal processor discharge chamber located downstream of the thermal processor for receiving the cooked MSW from the thermal processor and for providing a plug of cooked MSW at the outlet of the thermal processor, the thermal processor discharge chamber having a push floor feeder at its base for directing MSW out of the apparatus.

6. An apparatus as claimed in claim 4, comprising stoking means for maintaining the plug of MSW.

7. An apparatus as claimed in claim 1 comprising a shredder.

8. A apparatus as claimed in claim 1, wherein the agitating means for mixing the MSW in the drum or processor comprises means for rotating the drum or processor.

9. An apparatus as claimed in claim 8, wherein the agitating means comprises a tilting mechanism for tilting the drum or processor.

10. An apparatus as claimed in claim 1, wherein the wet-feed preparation drum is adapted to be inclined with respect to horizontal plane whereby entrance to the drum is in a lower plane that exit to the drum.

11. An apparatus as claimed in claim 1, wherein the drum or processor comprises internal lifting blades.

12. An apparatus as claimed in claim 1, the interior of said thermal processor tapers inwardly towards its exit.

13. An apparatus as claimed in claim 1, comprising an explosion vent for said thermal processor.

14. An apparatus as claimed in claim 1, comprising venting means adapted to remove excess heat and steam from the apparatus.

15. An apparatus as claimed in claim 14, wherein said venting means returns said excess steam to said moisture supply.

16. An apparatus as claimed in claim 14, comprising a scrubber for cleaning said excess steam.

17. An apparatus as claimed in claim 14, comprising an air separator for removal of any entrained airborne matter from said vented heat and steam.

18. An apparatus as claimed in claim 1, comprising means for heating the moisture supply.

19. An apparatus as claimed in claim 1, wherein the moisture evaporation means is a source of hot gases.

20. An apparatus as claimed in claim 1, comprising tilting means for adjusting the tilt of the drum and/or processor.

21. A process for treating municipal solid waste (MSW) comprising the steps of:
adding moisture to the MSW;
conveying the MSW through a non-pressurized feed preparation drum;
agitating said MSW as it is conveyed though the drum to moisten the MSW and to initilize pulping of organic matter present in the MSW;
conveying the moistened MSW from the drum to a non-pressurized thermal processor;
agitating said MSW as it is conveyed through the thermal processor; and
heating the moist MSW in the processor to substantially turn the moisture to steam to cook the MSW.

22. A process as claimed in claim 21, comprising the additional step of stocking the moistened MSW upon exit from the feed preparation drum to provide a plug of MSW at entrance to the thermal processor.

23. A process as claimed in claim 20, comprising the additional step of stocking the cooked MSW upon exit from the thermal processor to provide a plug of MSW at outlet of the thermal processor.

24. A process as claimed in claim 20, comprising the step of shredding and homogenizing the MSW before conveying it through the feed preparation drum.

25. A process as claimed in claim 24, wherein the MSW is shredded to have no dimension greater than 200 mm.

26. A process as claimed in claim 20, comprising the additional step of heating the moisture before it is added to the MSW.

27. A process as claimed in claim 20, the step of heating is heating the MSW to up to 400° C. at the outlet to the thermal processor and up to 100° C. at the inlet to the thermal processor.

28. A process as claimed in claim 20, comprising the step of monitoring the MSW in the various stages of the process and adjusting the rate of conveying the MSW based on the level of the MSW at a selected stage of the process.

* * * * *